(12) United States Patent
De Brouwer et al.

(10) Patent No.: US 11,145,421 B2
(45) Date of Patent: Oct. 12, 2021

(54) SYSTEM AND METHOD FOR REMOTE MEDICAL INFORMATION EXCHANGE

(71) Applicant: Sharecare AI, Inc., Palo Alto, CA (US)

(72) Inventors: Walter Adolf De Brouwer, Los Altos, CA (US); Srivatsa Akshay Sharma, Palo Alto, CA (US)

(73) Assignee: Sharecare AI, Inc., Palo Alto, CA (US)

( * ) Notice: Subject to any disclaimer, the term of this patent is extended or adjusted under 35 U.S.C. 154(b) by 0 days.

(21) Appl. No.: 16/802,485

(22) Filed: Feb. 26, 2020

(65) Prior Publication Data

US 2020/0279659 A1    Sep. 3, 2020

Related U.S. Application Data

(63) Continuation-in-part of application No. 15/946,629, filed on Apr. 5, 2018, now Pat. No. 11,026,634.

(60) Provisional application No. 62/810,549, filed on Feb. 26, 2019, provisional application No. 62/883,070, filed on Aug. 5, 2019, provisional application No. 62/942,644, filed on Dec. 2, 2019, provisional (Continued)

(51) Int. Cl.
*G16H 80/00* (2018.01)
*G16H 50/30* (2018.01)
*G16H 50/20* (2018.01)
*G16H 40/67* (2018.01)

(52) U.S. Cl.
CPC .............. *G16H 80/00* (2018.01); *G16H 40/67* (2018.01); *G16H 50/20* (2018.01); *G16H 50/30* (2018.01)

(58) Field of Classification Search
CPC ........ G16H 80/00; G16H 50/30; G16H 50/20; G16H 40/67; G16H 20/10; G16H 20/60; G16B 50/20
USPC ........................................................ 382/156
See application file for complete search history.

(56) References Cited

U.S. PATENT DOCUMENTS 8,543,428 B1 * 9/2013 Jones, III ............... G06Q 40/08
                                                                 705/4
9,839,376 B1 * 12/2017 Ross ....................... A61B 5/742
(Continued)

OTHER PUBLICATIONS

Yusuf, "Face-to-BMI: Using Computer Vision to Infer Body Mass Index on Social Media", Proceedings of the Eleventh International AAAI Conference on Web and Social Media, pp. 572-575 (ICWSM 2017). 2017.*

(Continued)

*Primary Examiner* — Juan A Torres
(74) *Attorney, Agent, or Firm* — Haynes Beffel & Wolfeld LLP; Mark A. Haynes; Sikander M. Khan

(57) ABSTRACT

Method and system for remote medical information exchanging are disclosed. The system for remote medical information exchanging comprises a computer application program and a data storage server. The computer application program is electrically coupled with a data storage server via communication network, comprising an end user end, configured to capture video stream of face of the end user; and a doctor end, configured to show the video stream of the face of end user and one or more physiological inference in accordance with the video stream. The data storage server, configured to store a scalable video server module, one or more artificial intelligence modules, a poly-omics uni-matrix pipeline, and a combined inference module.

1 Claim, 3 Drawing Sheets

Related U.S. Application Data application No. 62/975,177, filed on Feb. 11, 2020, provisional application No. 62/481,691, filed on Apr. 5, 2017.

(56) References Cited

U.S. PATENT DOCUMENTS

| | | | | |
|---|---|---|---|---|
| 2011/0172499 | A1* | 7/2011 | Simons-Nikolova | G16H 10/20 600/300 |
| 2011/0291834 | A1* | 12/2011 | Boldyrev | G06Q 20/363 340/572.1 |
| 2012/0162404 | A1* | 6/2012 | Howell | G16H 30/20 348/77 |
| 2013/0046761 | A1* | 2/2013 | Soderberg | G06Q 10/10 707/736 |
| 2015/0213207 | A1* | 7/2015 | Amarasingham | G16H 40/20 705/2 |
| 2015/0324686 | A1* | 11/2015 | Julian | G06N 20/00 706/25 |
| 2015/0339523 | A1* | 11/2015 | Tsunematsu | H04N 5/23206 382/103 |
| 2016/0253549 | A1* | 9/2016 | Ramie | G06K 9/00281 382/118 |
| 2017/0206691 | A1 | 7/2017 | Harrises et al. | |
| 2018/0289334 | A1* | 10/2018 | De Brouwer | A61B 5/7275 |
| 2019/0082211 | A1 | 3/2019 | Vats | |

OTHER PUBLICATIONS

Lingyun, "A computational approach to body mass index prediction from face images". Image and Vision Computing 31 (2013) pp. 392-400. 2013.*

U.S. Appl. No. 15/946,629—Office Action dated May 20, 2020, 10 pages.

U.S. Appl. No. 15/946,629—Response to Office Action dated May 20, 2020, filed Aug. 20, 2020,13 pages.

U.S. Appl. No. 15/946,629—Office Action dated Oct. 23, 2020, 9 pages.

U.S. Appl. No. 15/946,629—Notice of Allowance dated Jan. 22, 2021, 16 pages.

* cited by examiner

SYSTEM AND METHOD FOR REMOTE MEDICAL INFORMATION EXCHANGE

PRIORITY APPLICATIONS

This application claims priority to or the benefit of US Provisional Patent Application Nos. 62/883,070 titled, "ACCELERATED PROCESSING OF GENOMIC DATA AND STREAMLINED VISUALIZATION OF GENOMIC INSIGHTS," filed Aug. 5, 2019; U.S. Provisional Patent Application No. 62/942,644, titled, "SYSTEMS AND METHODS OF TRAINING PROCESSING ENGINES," filed Dec. 2, 2019; U.S. Provisional Patent Application No. 62/975,177, filed Feb. 11, 2020, titled, "ARTIFICIAL INTELLIGENCE-BASED DRUG ADHERENCE MANAGEMENT AND PHARMACOVIGILANCE,"; U.S. Provisional Patent Application No. 62/810,549, titled, "SYSTEM AND METHOD FOR REMOTE MEDICAL INFORMATION EXCHANGE," filed Feb. 26, 2019; This application is a continuation-in-part of U.S. patent application Ser. No. 15/946,629, entitled "IMAGE-BASED SYSTEM AND METHOD FOR PREDICTING PHYSIOLOGICAL PARAMETERS," filed on Apr. 5, 2018, which claims the benefit of U.S. Provisional Application No. 62/481,691, entitled "METHOD OF BODY MASS INDEX PREDICTION BASED ON SELFIE IMAGES," filed on Apr. 5, 2017. The provisional and non-provisional applications are hereby incorporated by reference for all purposes.

INCORPORATIONS

The following materials are incorporated by reference as if fully set forth herein:

U.S. Provisional Patent Application No. 62/883,639, titled "FEDERATED CLOUD LEARNING SYSTEM AND METHOD," filed on Aug. 6, 2019;

U.S. Provisional Patent Application No. 62/816,880, titled "SYSTEM AND METHOD WITH FEDERATED LEARNING MODEL FOR MEDICAL RESEARCH APPLICATIONS," filed on Mar. 11, 2019;

U.S. Provisional Patent Application No. 62/671,823, titled "SYSTEM AND METHOD FOR MEDICAL INFORMATION EXCHANGE ENABLED BY CRYPTO ASSET," filed on May 15, 2018; and U.S. Nonprovisional patent application Ser. No. 16/167,338, titled "SYSTEM AND METHOD FOR DISTRIBUTED RETRIEVAL OF PROFILE DATA AND RULE-BASED DISTRIBUTION ON A NETWORK TO MODELING NODES," filed on Oct. 22, 2018.

TECHNICAL FIELD

The disclosed system and method are in the field of information technologies to exchange medical information remotely.

BACKGROUND

Recent years, patients and plain consumers are getting more and more educated about personal health care and medical information. Generations with smartphones, which is almost all population in developed countries and growing population in developing countries, are enabled to check, collect, gather medical and health care information and data like never before. On the other hand, health and medical companies are having issues scaling their services, there are not enough physicians and family doctors, there are not enough nurses, and there are not enough genetic counselors. Existing technologies are ready for us to help health and medical services suppliers to scale customer supports. The strong development in artificial intelligence in natural language understanding and processing makes it possible for us to teach our machines augment medical and health care services in a dramatic way.

Telehealth, i.e., health care services via telecommunications or similar, is becoming a popular alternative to the make up for the lack of general practitioners, genetic counsellors, and in general to scale care.

Most of the Telehealth solutions today require doctors to make a vision inspection patient over a video feed and infer all the medical information via a dialog with the patient remotely. There are a few setbacks that make Telehealth not the most efficient form of care.

One of the setbacks is that doctors do not have the same level of visibility to a patient's facial expression, feeling, or sentiments as compared to in person. A lot of diagnosis depends on how the patient looks, feels, and behaves that physicians are trained to read as cues for diagnostics. Secondly, doctors can miss asking relevant question as the necessary context can be missing in a remote set-up. Thirdly, it is also harder for patients to provide all the requisite medical history including modern type of data like genetic data, microbiome data, or lab results to the doctor effectively over a video feed. Therefore, in the end, the diagnostics provided over Telehealth is not as effective as in-person consultation.

In the present disclosure, system and method for remote medical information exchange are to be discussed.

SUMMARY

Generally provided are a system and method for remote medical information exchanging by a telehealth augmentation platform. The system for medical information exchanging can be used directly via phenomenal face mobile application program as well as embedded into other compatible platforms that support telehealth. With Phenomenal Telehealth Augmentation doctors are provided auto inferred medical information about the patient while having the video conversation. This enables the doctors and physicians to make better decision and converge to the right conversations quickly in order to provide better diagnostics. Some examples of the type of inference that is provided during the video feed can include auto inference of age, sex, height, weight, auto inference of mood and sentiment to reflect how the patient feels, auto inference of recommended screenings and diagnostics, auto inference of exposome data like air quality, pollen exposure, socio-economic risks, etc. based on the location from where the user is connecting, auto inference of risks for genetic diseases if the patient has uploaded genetic data, auto inference of past medical records and past prescriptions using camera to capture this information.

This summary is provided to efficiently present the general concept of the invention and should not be interpreted as limiting the scope of the claims.

BRIEF DESCRIPTION OF THE DRAWINGS

For purpose of facilitating understanding of the embodiments, the accompanying drawings and description illustrate embodiments thereof, its various structures, construction, method of operation, and many advantages that may be understood and appreciated. According to common practice, the various features of the drawings are not drawn to scale.

DETAILED DESCRIPTION

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more embodiments may also be included in combination with another embodiment even though not expressly shown and described in that specific combination.

For purpose of efficiency, reference numbers may be repeated between figures where they are intended to represent similar features between otherwise varied embodiments, though those features may also incorporate certain differences between embodiments if and to the extent specified as such or otherwise apparent to one of ordinary skill, such as differences clearly shown between them in the respective figures.

Figure 1:
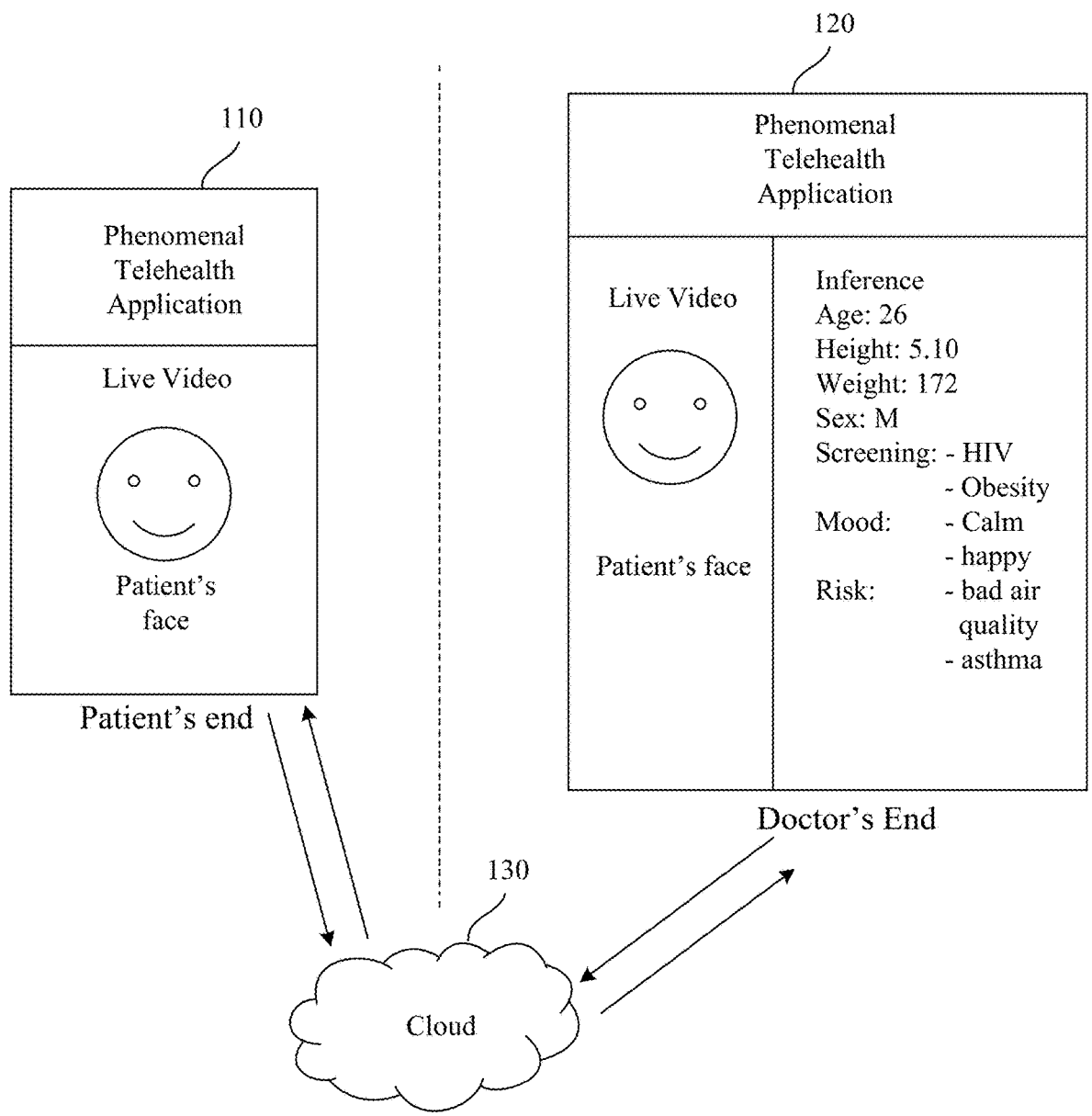
FIG. 1 is a diagram illustrating an exemplary information exchange scenario for the applications of healthcare services and clinical and/or data trials, consistent with embodiments of the present disclosure.

Reference is now made to FIG. 1, which is a diagram illustrating an exemplary information exchange scenario for the applications of healthcare services and clinical and/or data trials, consistent with embodiments of the present disclosure.

Patient or end user uses a phenomenal telehealth application program to connect to a virtual telehealth consultation session. The phenomenal telehealth application can be installed at an electronic device 110 at the patient or end user's end, a mobile device, e.g. a mobile phone, a tablet, etc., and can also be installed at a computer connected to internet or a secured network. A doctor or physician uses the application program to connect to the virtual telehealth consultation session, from the doctor or physician's end via an electronic device 120, e.g., a mobile device or ideally a computer connected to internet or a secured network. In some embodiments, the phenomenal telehealth application can be integrated and embedded into other third party telehealth application or platform using a telehealth license module. The phenomenal telehealth application does not necessarily run on its own or stand alone.

In some embodiments, medical or health related data and information of the patient or end user can be received by the exchange platform and stored in a remote and secured data storage center with cloud services 130, e.g., Google Cloud, Amazon AWS, Microsoft Azure Cloud, or other cloud services. There are one or more auto inference machine learning modules preinstalled in data storage center with cloud services 130.

At the patient or end user's end, patient or end user's face is to be captured by camera of electronic device 110 in a live video form. Via data storage center with cloud services 130 and communication network, the live video stream is to be sent to the doctor or physician's end and shown on screen of electronic device 120. At the same time, on the screen of electronic device 120, the inference results derived by auto inference machine learning modules are shown at another portion of the screen.

In some embodiments, the inference results can include various physiological parameters of the patient or end user undergoing the virtual telehealth consultation session. These physiological parameters include but not limited to age, height, weight, sex, screening, mood, risks, etc. All the physiological parameters are real-time derived and reflect the individual information of the patient or end user. Such physiological parameters are augment to the facial live video stream. The inference information significantly reduces the time required for the doctor to understand the patient's basic essentials as well as other information that might be missed due to the lack of in person context. This will also drive the conversation to more of an individualized feeling level and focus on the patient's problem instead of wasting time on less essential information.

Figure 2:
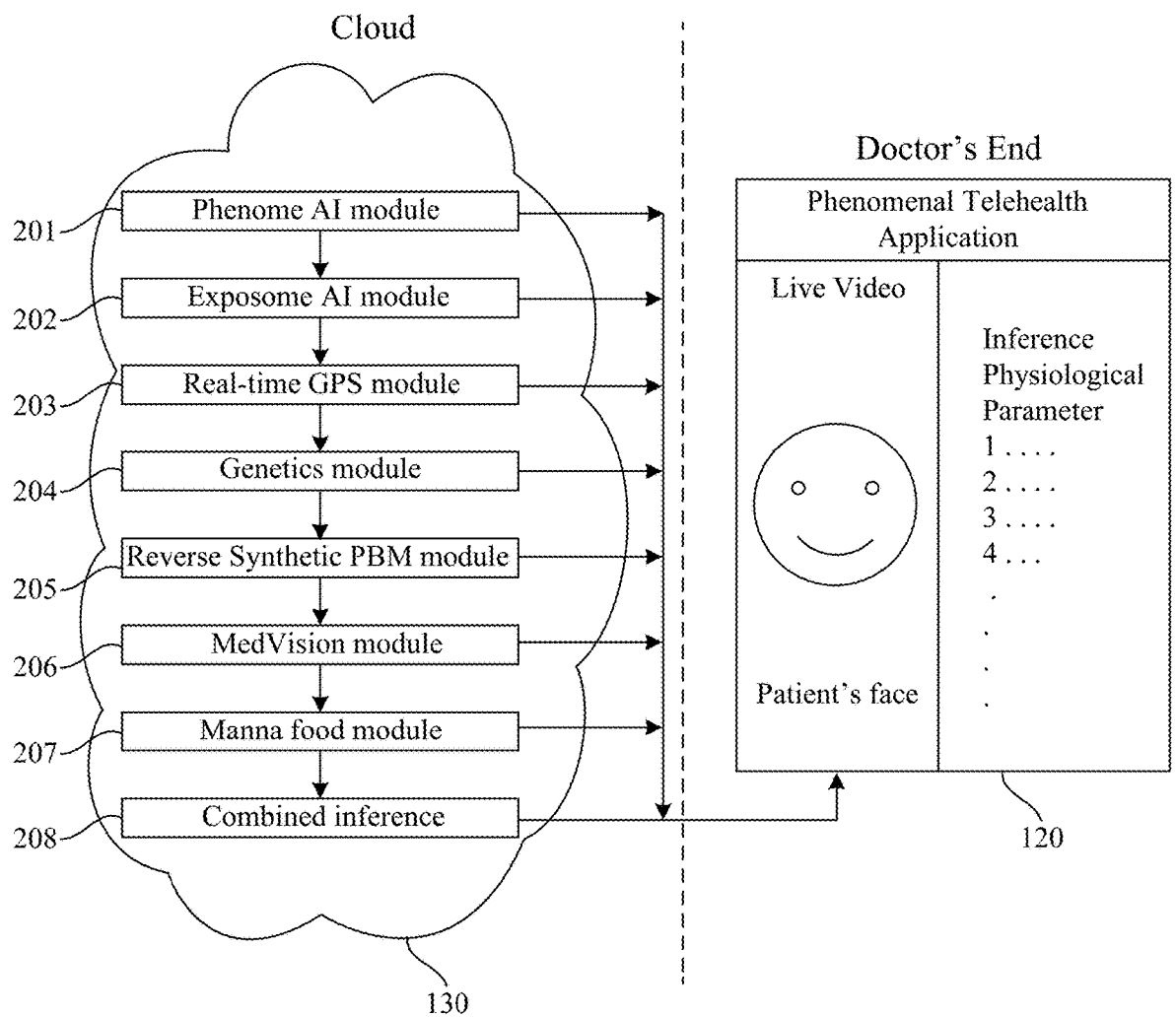
FIG. 2 is a diagram illustrating an exemplary data storage center with cloud services and its machine learning modules, as well as the interaction between live video stream with these machine learning modules, consistent with embodiments of the present disclosure.

Reference is now made to FIG. 2, which is a diagram illustrating an exemplary data storage center with cloud services and its machine learning modules, as well as the interaction between live video stream with these machine learning modules, consistent with embodiments of the present disclosure.

When the live video stream is streamed up to data storage center with cloud services 130, machine learning modules pre-installed in the cloud start analyzing the live video stream. In some embodiments, machine learning module can include but not limited to phenome artificial intelligence module 201, exposome artificial intelligence module 202, real-time Global Position System (GPS) or navigation module 203, genetics and bioinformatics module 204, reverse synthetic Pharmacy Benefit Manager (PBM) module 205, MedVision module 206, Manna food module 207, predictions machine module 208, etc. The pre-installed machine learning modules can be one or more of any combination of the aforementioned modules. Each machine learning module functions as its name indicates. A combined and cross-referenced inference physiological information is to be streamed to electronic device 120 at the doctor or physician's end and shown on the screen.

Figure 3:
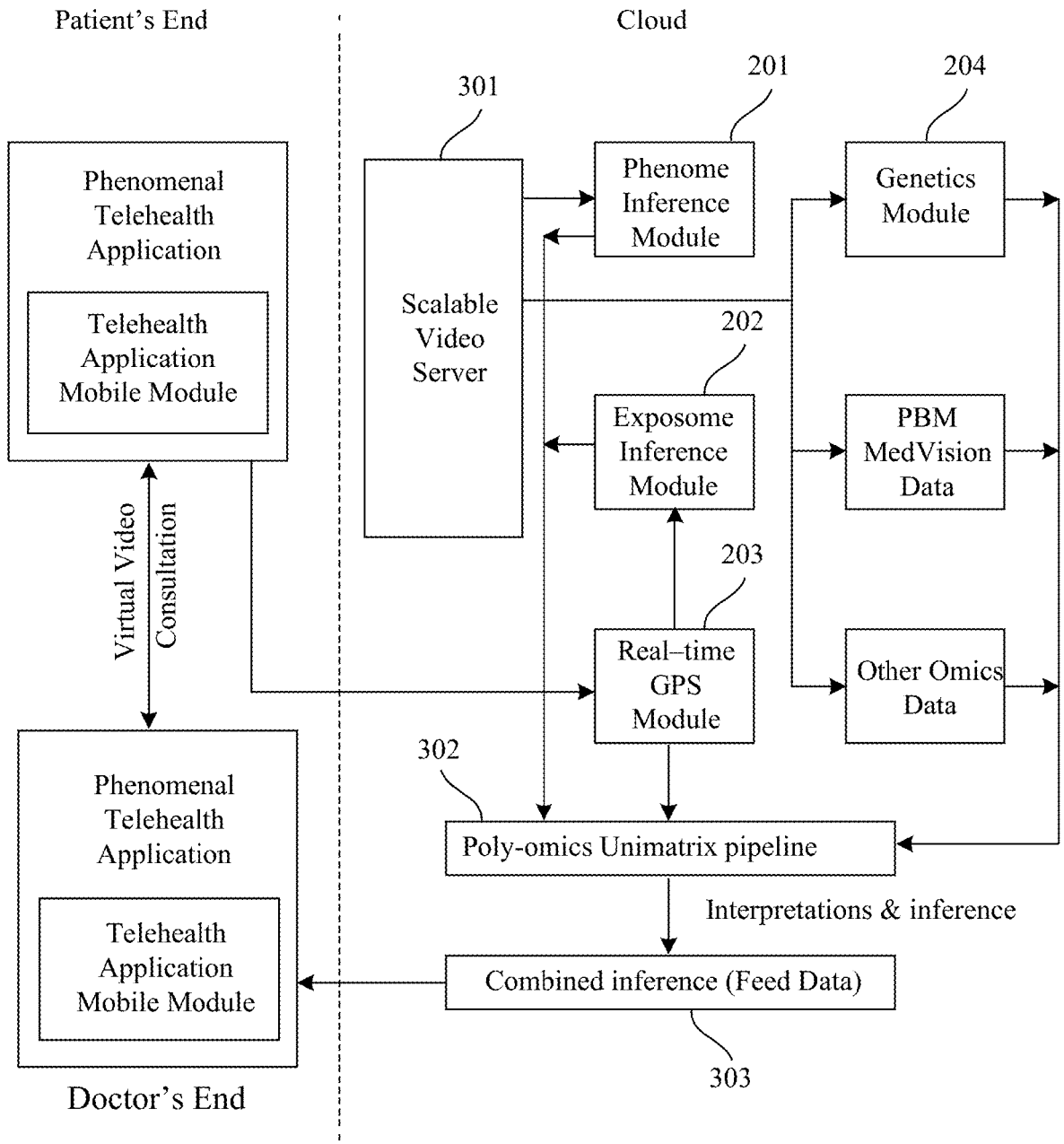
FIG. 3 is a diagram illustrating an exemplary system architecture of data storage center with cloud services, consistent with embodiments of the present disclosure.

Reference is now made to FIG. 3, which is a diagram illustrating an exemplary system architecture of data storage center with cloud services, consistent with embodiments of the present disclosure.

The system is largely a composable set of backend artificial intelligence-based modules that uses data from software development kit and/or from telehealth application program to make a combined prediction for virtual consultation session. In some embodiments, the system services comprise scalable video server 301, phenome artificial intelligence inference module 201, real-time GPS module 203, exposome artificial intelligence inference module 202, genetics and bioinformatics module 204, reverse synthetic PBM module, MedVision module, Manna food module, poly-omics uni-matrix pipeline 302, and combined inference module 303.

Scalable video server 301 ingests the live video stream of the patient or end user during the virtual consultation session for interpretations by doctor or physician.

Scalable video server 301 is configured to ensure the user's privacy is preserved and it is via an opt-in with consent from the patient or end user. It is also configured to high security to facilitate one on one video conversation. Phenome artificial intelligence inference module 201 is configured to extract facial data and infers physiological parameters including age, sex, height, weight, BMI, mood, life-expectancy, or other statistical measures. Real-time GPS module 203 is configured to constantly synchronize to the patient or end user's physical location and past locations in order to understand the exposimics of the user. Exposome artificial intelligence inference module 202 is configured to compute the risks and exposures to air quality, pollen, walkability (how active one is allowed in the condition), socio-economic risks, etc. Inference data from this module augments the risk for certain medical conditions, e.g., Asthma, allergies, etc., that a doctor or physician should be aware of. Further description of these modules is found in ARTIFICIAL INTELLIGENCE-BASED DRUG ADHERENCE MANAGEMENT AND PHARMACOVIGILANCE, incorporated above by reference.

Genetics and bioinformatics module 204 is configured to allow a patient or end user upload his/her genetic profile data, from consumer faced genetic services such as 23andMe, Ancestry, full exome sequence, whole genome sequence, etc., as part of the application program onboarding procedure. Further description of handling and analysis of genetic information if found in ACCELERATED PROCESSING OF GENOMIC DATA AND STREAMLINED VISUALIZATION OF GENOMIC INSIGHTS and ARTIFICIAL INTELLIGENCE-BASED DRUG ADHERENCE MANAGEMENT AND PHARMACOVIGILANCE, incorporated above by reference. The information collected by genetic and bioinformatics module can be used along with the combination of other phenotypic data from phenome artificial intelligence inference module 201. Reverse synthetic pharmacy benefit manager (PBM) module is configured to allow patient or end user to optionally add medications and prescription information using the MedVision module. Further description of PBM and MedVision modules is found in ARTIFICIAL INTELLIGENCE-BASED DRUG ADHERENCE MANAGEMENT AND PHARMACOVIGILANCE, incorporated above by reference. The reverse synthetic PBM module curates the drug information for patient or end user. Such drug information can also be cross-referenced with genetics data to red flag risks of certain drugs to patient or end user.

MedVision module is configured to allow patient or end user to import his/her medical records and medication information by using the camera of electronic device 110. Patient and end user can use the cameral of electronic device 110 to take a picture over medications he/she takes. MedVision module 206 is configured to process the image to capture the medication information. Manna food module 207 is configured to estimate the probability that food in a picture is scientifically considered to be healthy or not. Polyomics uni-matrix pipeline 302 is configured to be fed by data from some or all aforementioned artificial intelligence modules. It joins multiple omics collected to build predictive values on the patient or end user in a real-time manner. Further description of polyomics is found in ARTIFICIAL INTELLIGENCE-BASED DRUG ADHERENCE MANAGEMENT AND PHARMACOVIGILANCE, incorporated above by reference. Combined inference module 303 is configured to combine all the predictions and inferences from some or all modules. Display feed data formed by combined inference module 303 is to be passed back to doctor's end of phenomenal telehealth application.

Although the invention is illustrated and described herein with reference to specific embodiments, the invention is not intended to be limited to the details shown. Rather, various modifications can be made in the details within the scope of equivalents of the claims by anyone skill in the art without departing from the invention.

The ability for a doctor or physician to get auto inferred information while keeping the patient or end user highly engaged on a video stream is a groundbreaking change for Telehealth. It allows doctors and physicians to focus on having scientifically and medically more meaningful conversation with patients or end users on medical problems instead of frivolous data collection.

Most importantly, as patient or end user adds additional data into the phenomenal telehealth application, the information is correlated and used for building better predictions. The confluence of all data from end user and context means that doctor or physician doesn't have to do administrative work of data collection during a patient's consultation, thus saving a lot of time and being more effective providing diagnostics.

In the following claim, the modules can be used by themselves, in pairs, in triplets and in other combinations. Not all of the modules need to be used to compose a functional and beneficial system. This applies as well to methods and CRMs that practice the technology disclosed.

The technology disclosed also can be practiced as a method or non-transitory computer readable medium. As a method, the technology disclosed exercises the functions indicated by the various modules, as described herein and in the materials incorporated by reference. As a CRM, the technology disclosed includes computer program instructions that, when combined with computer hardware, result in a system as described with various modules, as described herein and in the materials incorporated by reference. Alternatively, as a CRM, the technology disclosed includes computer program instructions that, when executed on one or more processors coupled to memory, displays, a network interface, etc., exercises the functions indicated by the various modules, as described herein and in the materials incorporated by reference.

We claim as follows:

1. A system for remote medical information exchanging, comprising:
   a computer application program, electrically coupled with a data storage server via communication network, comprising
   an end user end, configured to capture video stream of face of the end user; and
   a doctor end, configured to show the video stream of the face of end user and one or more physiological inference in accordance with the video stream;
   a data storage server, configured to store a scalable video server module, one or more artificial intelligence modules, a polyomics uni-matrix pipeline, and a combined inference module, wherein the one or more artificial intelligence modules comprise one, two, three, four or more of the following modules,
   a phenome artificial intelligence module, configured to extract facial data and infers physiological parameters;
   an exposome artificial intelligence module, configured to configured to compute the risks and exposures to environment;

a real-time global position system module, configured to synchronize to the end user's physical location;
a genetics and bioinformatics module, configured to allow end user to upload genetic profile data;
a MedVision module, configured to capture images of medication and prescription image of end user;
a reverse synthetic pharmacy benefit manager module, configured to allow end user to add medications and prescription information; and
a Manna food module, configured to decide food in an image is healthy or not.

\* \* \* \* \*